United States Patent [19]

Gupton et al.

[11] 4,344,429
[45] Aug. 17, 1982

[54] BUBBLE DETECTOR WITH FEEDBACK CIRCUIT FOR IMPROVED SENSITIVITY

[75] Inventors: John E. Gupton, Vernon Hills; Norman Shim, Glenview, both of Ill.

[73] Assignee: Baxter Travenol Laboratories, Inc., Deerfield, Ill.

[21] Appl. No.: 103,057

[22] Filed: Dec. 13, 1979

[51] Int. Cl.$^3$ .................. A61M 5/14; G08B 21/00
[52] U.S. Cl. .................. 128/214 R; 128/214 C; 128/214 E; 250/574; 250/564; 250/565; 250/204
[58] Field of Search .......... 128/214 R, 214 C, 214 E, 128/633, 395, 214 B; 250/574, 204, 564, 565

[56] References Cited

U.S. PATENT DOCUMENTS

| | | | |
|---|---|---|---|
| 3,177,757 | 4/1965 | Polanyi | 250/574 |
| 3,192,473 | 6/1965 | Marsh | 128/DIG. 13 |
| 3,461,856 | 8/1969 | Polanyi | 128/633 |
| 3,518,437 | 6/1970 | Riggs | 250/574 |
| 3,618,061 | 11/1971 | Livers | 340/236 |
| 3,935,876 | 3/1976 | Massie et al. | 128/214 E |
| 3,987,303 | 10/1976 | Stoft et al. | 128/633 |
| 4,003,707 | 1/1977 | Lübbers et al. | 128/633 |
| 4,014,010 | 3/1977 | Jinotti | 128/214 E |
| 4,038,982 | 8/1977 | Burke et al. | 128/214 |
| 4,075,462 | 2/1978 | Rowe | 235/92 |
| 4,114,144 | 9/1978 | Hyman | 340/632 |

Primary Examiner—Kyle L. Howell
Assistant Examiner—Nancy A. B. Swisher
Attorney, Agent, or Firm—John P. Kirby, Jr.; Eugene M. Cummings; Bradford R. L. Price

[57] ABSTRACT

In a flow metering apparatus, a bubble detector for detecting bubble formation in tubing includes a light source and first and second light detectors. The first light detector is positioned on the opposite side of the tubing from the light source such that the light transmitted through the tubing to the detector is dependent on the focusing effect of fluid in the lumen of the tubing. A control circuit responsive to the output of the detector interrupts operation of the metering apparatus when the light transmitted through the tubing falls below a predetermined minimum level. The second light detector is positioned at an angle to the light path between the light source and the first detector so as to receive increased light from the light source in the absence of the focusing effect of fluid in the tubing. Intensity control means responsive to the output of the light source with increased incident light at the second detector to increase the responsiveness of the bubble detector to the absence of fluid in the tubing.

7 Claims, 8 Drawing Figures

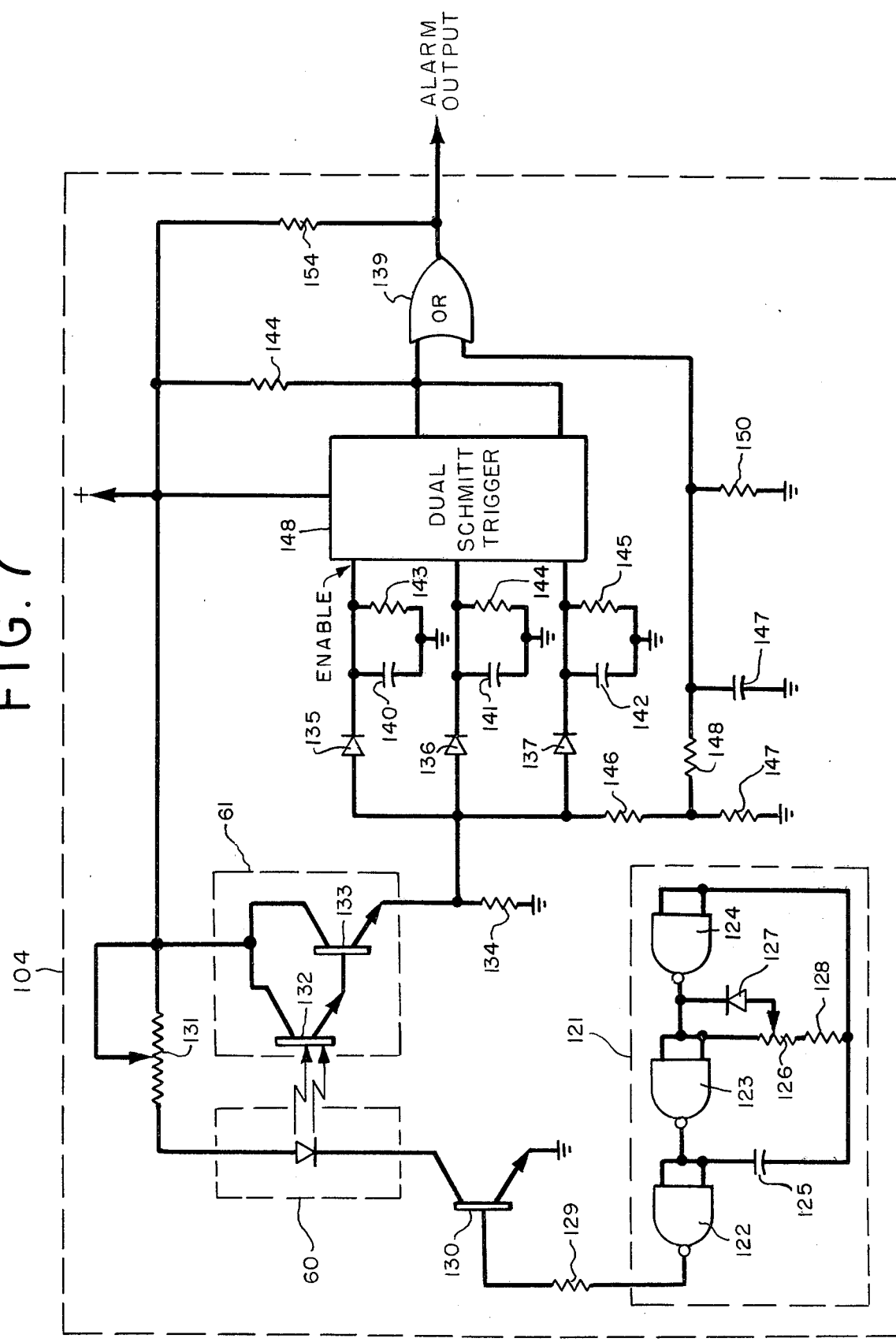

BUBBLE DETECTOR WITH FEEDBACK CIRCUIT FOR IMPROVED SENSITIVITY

BACKGROUND OF THE INVENTION

The present invention relates generally to fluid infusion systems, and more particularly to an improved apparatus for detecting the formation of bubbles in such systems.

The infusion of fluids such as parenteral fluids and blood into the human body is usually accomplished by means of an administration set and metering apparatus which controls the rate of flow of fluid through the set. Peristaltic-type pumps, which function by repetitively compressing and expanding a section of tubing, have proven particularly attractive for use in such metering apparatus since they do not introduce the possibility of leakage or contamination into the system, while providing positive control of fluid flow through the system. One form of metering apparatus employing a peristaltic-type pump is described in U.S. Pat. No. 4,155,362, which issued to Thurman S. Jess on May 22, 1979, and is assigned to the present assignee. A successful commercial embodiment of this apparatus is currently marketed as the Travenol Model 2M8014 infusion pump by Baxter Travenol Laboratories, Inc., of Deerfield, Ill.

One problem which arises with the use of fluid infusion sets is that dissolved gases in the liquid being infused may be released as bubbles as the liquid is subjected to pressure and/or temperature changes as it passes through the pump of the metering apparatus. These bubbles may coalesce and form larger bubbles or pockets of gas which may be infused along with the liquid into the body, an occurence which may be harmful or even fatal to the patient under certain circumstances.

To prevent gas from being infused it has become common practice to locate a bubble detector downline of the metering apparatus pump to automatically stop the apparatus should gas bubbles be detected. Such detectors typically employ a light source and a light detector positioned on opposite sides of the administration set tubing to monitor the level of light transmitted through the tubing. Operation of the metering apparatus is interrupted and an alarm is sounded when the transmitted light level falls below a predetermined level.

One preferred form of bubble detector utilizes the focusing or lens effect of the fluid in the lumen of the tubing to enhance the difference in light transmission levels through the tubing between fluid and no fluid conditions. The present invention is directed to an improvement in such systems whereby improved responsiveness to the absence of fluid in the tubing is achieved.

Accordingly, it is a general object of the present invention to provide a new and improved bubble detector.

It is another object of the present invention to provide a new and improved bubble detector having improved responsiveness to the absence of fluid in the tubing being monitored.

It is a further object of the present invention to provide a bubble detector wherein the lens effect of fluid within the lumen of the tubing being monitored is utilized to detect with improved responsiveness the absence of fluid within the tubing.

SUMMARY OF THE INVENTION

The invention is directed, in a flow metering apparatus for controlling the flow of fluid through an administration set of the type having transparent tubing, to a bubble detector comprising a light source arranged at one side of the tubing, and a first light detector generally arranged at the opposite side of the tubing and defining in conjunction with the light source a light path through the tubing. The first light detector generates a first output signal in response to the intensity of light from the light source incident thereon, the intensity of the incident light increasing in the presence of fluid within the lumen of the tubing as a result of the focusing effect thereof. A second light detector generally arranged at an angle to the light path is provided to generate a second output signal in response to the intensity of the light incident thereon, the intensity of the incident light decreasing in the presence of fluid within the lumen of the tubing as a result of the focusing effect thereof. Detector circuit means responsive to the first output signal are provided for interrupting operation of the flow metering apparatus upon the intensity of the light incident of the first light detector falling below a predetermined minimum level. Intensity control means responsive to the second detector output signal decreases the light output of the light source upon the light incident on the second detector increasing to increase the effectiveness of the control circuit means in responding to the absence of fluid in the lumen of the tubing.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, and the several figures of which like reference numerals identify like elements, and in which:

FIG. 7 is a simplified schematic diagram of a preferred detector circuit for use in conjunction with the bubble detector of the invention.

DESCRIPTION OF THE PREFERRED EMBODIMENT

Figure 1:
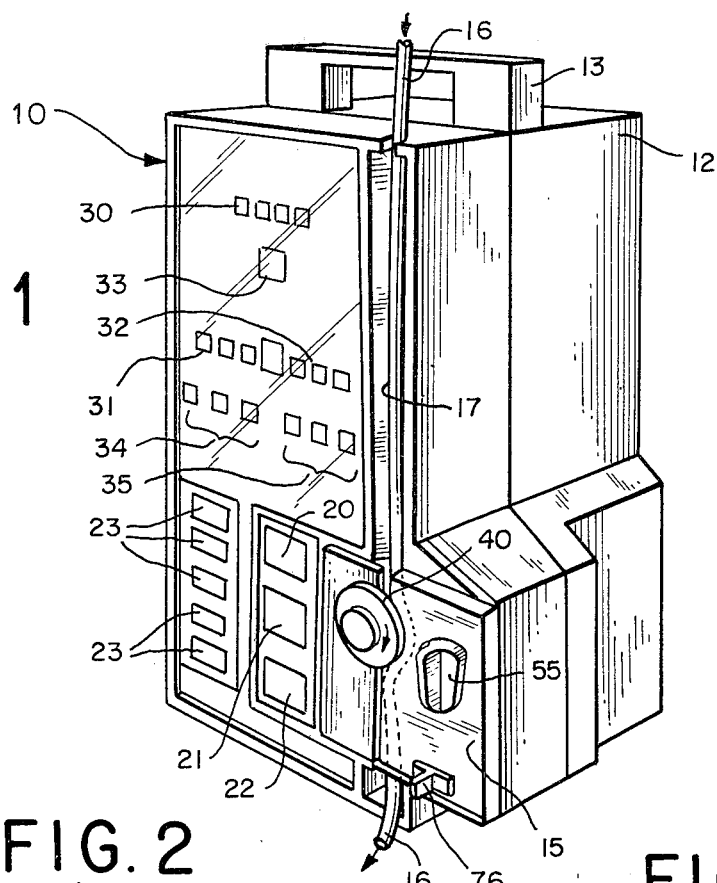
FIG. 1 is a perspective view of a metering apparatus incorporating a bubble detector constructed in accordance with the invention.

Referring to the figures, and particularly to FIG. 1, a peristaltic-type flow metering apparatus 10 for use in conjunction with an administration set for controlling the flow of fluid into a vein or artery includes a generally rectangular housing 12 having a handle 13 at one end thereof for convenient carrying. The front surface of the housing includes a control panel 14 which allows the operator to control and monitor the operation of the metering apparatus, and a peristaltic-type flow metering head 15 for compressing a section of tubing 16 of the administration set to effect control of fluid flow therein. A channel 17 is provided above the metering head 15 for maintaining a portion of the tubing segment in convenient view of the operator whereby flow irregularities can be more readily observed.

The administration set, of which tubing segment 16 is a part, and which may be conventional in design and construction, is preferably formed of a plastic material such as vinyl and packaged in a sterile and non-pyrogenic condition. To avoid the danger of contamination, the administration set is normally utilized for one application only, and is disposed of after a single use.

The operating mode of metering apparatus 10 is controlled by means of a push button STOP switch 20, a push button START switch 21, and a push button power ON-OFF switch 22. Each of these push button switches includes an internal indicator lamp which provides a positive indication of the operation of the operating mode of the apparatus. Various abnormal operating conditions are annunciated by means of indicator lights 23 contained on the control panel to the left (as viewed in FIG. 1) of the mode control push buttons.

Control panel 14 further includes a digital display 30 of volume infused, a digital display 31 of volume to be infused, and a digital display 32 of the fluid flow rate. The volume displayed by display 30 is the volume of fluid actually infused, and can be reset to zero by the operator by means of a push button RESET switch 33. The volume to be infused by display 31 is preset by the operator by means of a set of push button switches 34 to indicate a desired volume of fluid to be infused. Similarly, the infusion rate display 32 is preset by the operator by means of a second set of push button switches 35 to indicate the rate at which infusion is to take place.

The operation of the various indicators, control switches and other features of metering apparatus 10 is described in detail in the copending applications of Thurman S. Jess and Norm Shim, Ser. No. 856,863; Norm Shim, Ser. No. 857,018; Norm Shim and Vincent L. Knigge, Ser. No. 856,927; and Thurman S. Jess, Ser. No. 856,926; all filed Dec. 2, 1977.

Figure 2:
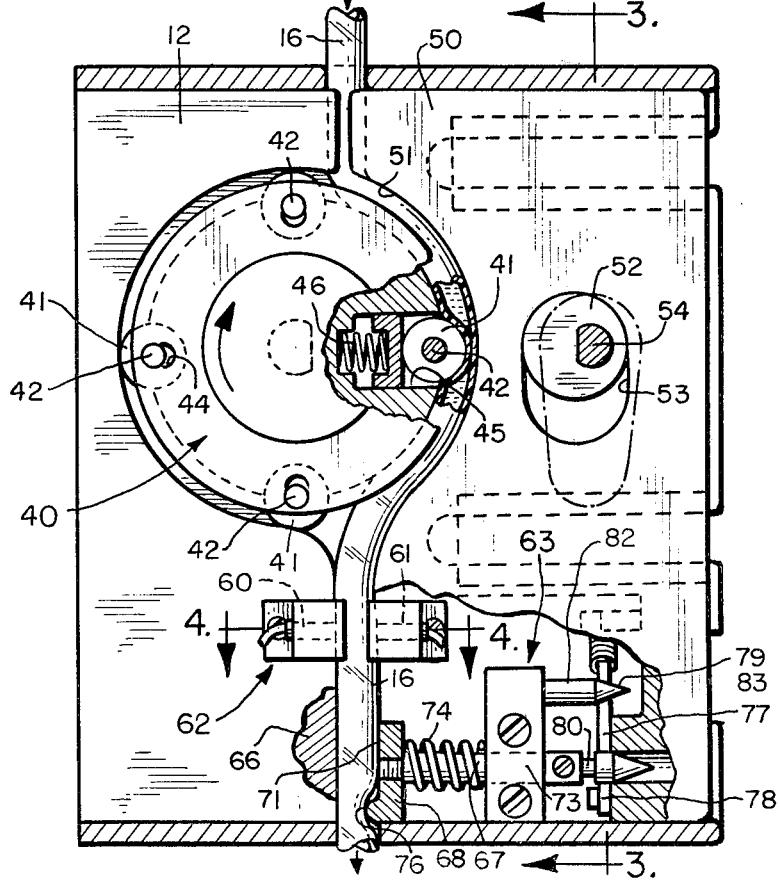
FIG. 2 is an enlarged front elevational view of the metering station of the flow metering apparatus partially in section and partially broken away to illustrate the operation thereof.
Figure 3:
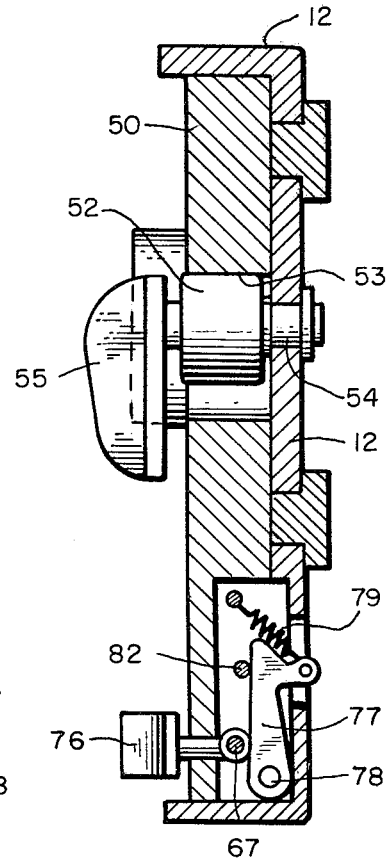
FIG. 3 is a cross-sectional view of the metering station taken along line 3—3 of FIG. 2.

Referring to FIGS. 2 and 3, the peristaltic metering head 15 includes a rotor 40 having four pressure rollers 41 disposed in equi-spaced relation about its circumference. The rollers are each mounted on a shaft 42 for free rotation, and the shafts are carried on carriages 43 and constrained to radial movement by respective radial slots 44. Each carriage is mounted for reciprocation within a radial recess 45 and spring loaded radially outward by a helical spring 46 disposed within the recess.

The pump also includes a pressure plate 50 having an arcuate working surface 51 which substantially corresponds in shape to the circumference of rotor 40. The working surface brings tubing 16 into compressive engagement with rollers 41 around at least a portion of the rotor circumference corresponding to the spacing between adjacent rollers. The pressure plate may be reciprocated toward and away from rotor 40 to facilitate installation and removal of tubing 16 by rotation of an eccentric cam 52, which is contained to operate within a vertical slot 53 provided on the pressure plate. Rotation of the cam is accomplished by a shaft 54 and a user-actuable lever 55 operatively connected to the cam. When the lever 55 is in its vertical position, as shown in FIG. 3, the pressure plate is moved sufficiently close to the rotor circumference to cause tubing 16 to be completely occluded by one of the pressure rollers 41.

After passing through metering station 15, tubing 16 extends between a light source 60 and a light detector 61, which together comprise a bubble detector head 62. This head, combined with associated control circuitry, forms a bubble detector system which discontinues operation of the metering apparatus and alerts the operator upon formation of a bubble in the tubing.

The tubing next passes through a flow restriction station 63. This station includes a pressure block 66 and a slidably mounted plunger 67 biased against the sidewall of tubing segment 16. The end of plunger 67 which engages the tubing segment includes a generally L-shaped head portion 68 having a wedge-shaped working surface 70 which occludes the tubing and a generally flat control surface 71 which responds to fluid pressure changes. Plunger 67 is slidably received within a mounting block 73, and extends through the center of a helical compression spring 74 which biases head 68 into engagement with the tubing. The occlusion of the tubing by the flow restriction station increases the pressure of the fluid in the tubing at the point of engagement of the rollers 41 of rotor 40 to assist in restoration of the tubing following compression by the pressure rollers for improved metering accuracy.

Plunger 67 can be opened to facilitate loading or unloading of tubing 16 by means of a lever 76. The plunger is locked open by means of a latch member 77 which is pivotally mounted at 78 to pressure plate 50 and biased by a helical spring 79 for operation within a plane perpendicular to the plunger. Latch member 77 is received in a slot 80 on the plunger when the plunger is moved to its full open position.

To insure that plunger 67 will be released when pressure plate 50 is subsequently closed, an actuator pin 82 having a tapered end surface displaces latch member 77 from slot 80 when the pressure plate is returned to its closed position by rotation of knob 55. This prevents inadvertent operation of the system without the back pressure and gravity flow protection provided by the plunger. Also, when the pressure plate is opened, the displacement of latching member 77 prevents the plunger from being latched open.

Figure 4:
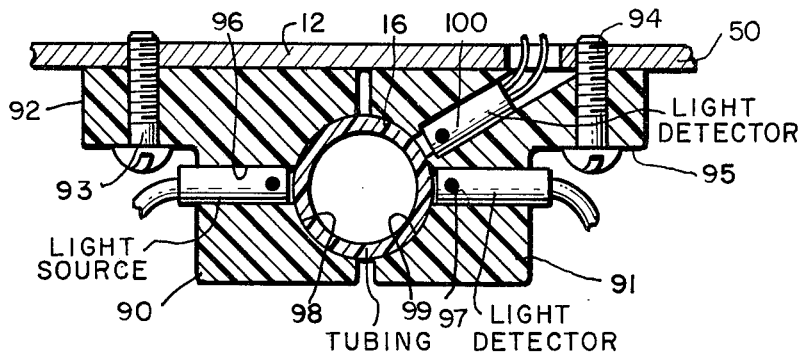
FIG. 4 is an enlarged cross-sectional view of the bubble detector head of the metering station taken along line 4—4 of FIG. 2.

Referring to FIG. 4, the detector head 62 is seen to comprise first and second forming members 90 and 91 disposed on opposite sides of tubing segment 16. The first form member 90 is secured to housing 12 by a bolt 93 extending through a flange portion 92. Similarly, the second form member 91 is secured to the slidable pressure plate 50 by means of a bolt 94 extending through a flange portion 95 of the base member.

To provide mounting means for light source 60, the first form member 90 is provided with a bore 96 perpendicularly aligned to the axis of tubing 16. To provide a receptacle for photodetector 61, form member 91 is similarly provided with a perpendicularly aligned bore 97. Bores 96 and 97 are each dimensioned with an inside diameter just slightly larger than the outside diameter of light source 96 and photodetector 97, respectively, to provide a fit for these elements sufficiently tight to maintain the elements in alignment.

It will be noted that form members 90 and 91 define inwardly concave mandrel surfaces 98 and 99, respectively, between which tubing 16 is held when the form elements 90 and 91 are in their closed position, as shown in FIG. 4. The curvature of these mandrel surfaces is dimensioned to correspond closely to the natural or unstressed curvature of the outside surface of tubing 16 so that when engaged to form members the tubing lumen is maintained in its unstressed cross-sectional shape notwithstanding pressure changes in the fluid contained therein. This feature is fully described in the copending application of Nick Zissimopoulous and John Baron, Ser. No. 103,040, filed concurrently herewith, now U.S. Pat. No. 4,312,341.

To remove the tubing, it is merely necessary to separate form members 90 and 91. In metering apparatus 10 this is accomplished automatically upon upon the operator actuating knob 55 to open metering station 15, since form member 90 is mounted to a stationary housing member, and form member 91 is mounted to the movable pressure plate 50.

Figure 5A:
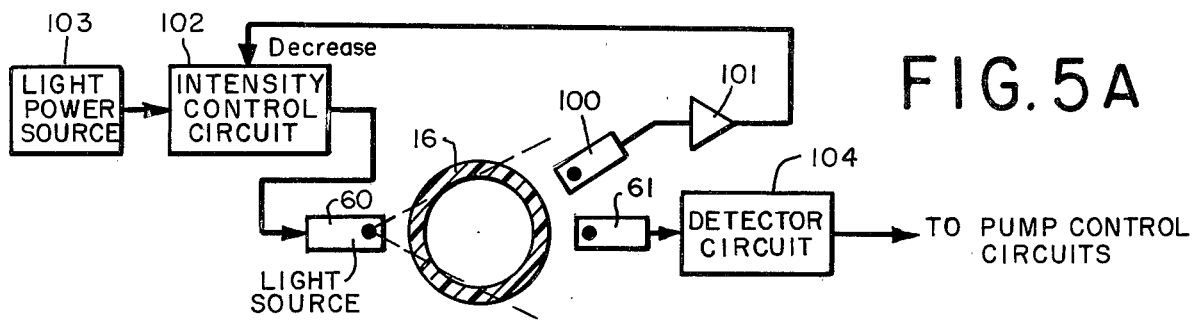
FIG. 5 (A) is a diagrammatic depiction of the bubble detector system of the metering apparatus useful in depicting operation of the system in the absence of fluid.
FIG. 5(B) is a diagramatic depiction similar to FIG. 5(A) showing operation of the bubble detector system with fluid present.
Figure 5B:
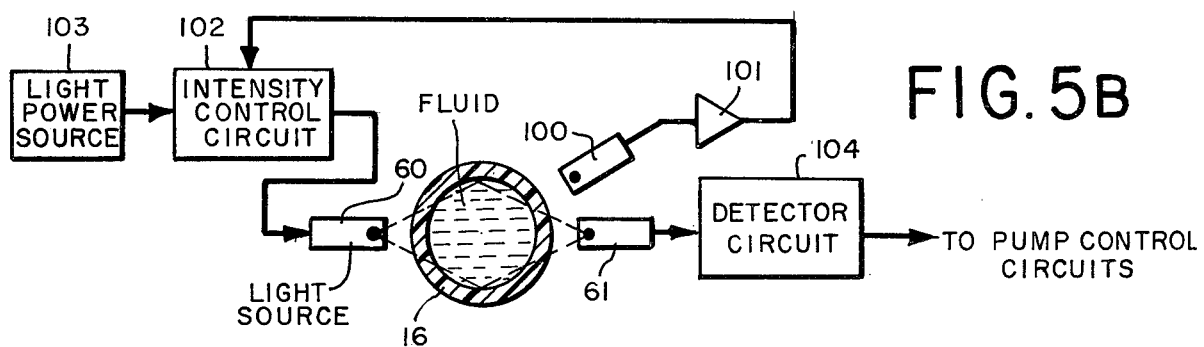

Referring to FIGS. 5(A) and 5(B), operation of the bubble detector is dependent on a focusing or lens effect produced by fluid in the lumen of the tubing. As shown in FIG. 5(A), in the absence of fluid light from light source 60 diverges as it passes through the transparent walls of the tubing. As a result, only a small portion of the light transmitted through the tubing actually falls upon light detector 61, and the resulting signal produced by that device is small. In contrast, when liquid is present in the lumen of the tubing as shown in FIG. 5(B), the circular cross-section of the fluid mass, as defined by the inner surface of the wall of the tubing, forms a lens which focuses the light on detector 61. As a result, a greater portion of the transmitted light is actually incident on the detector and the resulting detector output signal is stronger. By comparing the light detector output signals for the conditions shown in FIGS. 5(A) and 5(B), appropriate bubble detector circuitry within metering apparatus 10 determines the presence or absence of fluid in the tubing.

In accordance with the invention, the difference in incident light levels on light detector 91 between fluid and no fluid conditions is accentuated to obtain a more positive response upon detection of a bubble. This is accomplished by providing a second light detector 100 arranged generally at the opposite side of the tubing from the light source and aligned at an angle to the light path between light source 60 and detector 61 by the lens effect of tubing in the lumen. Thus, a greater amount of light is incident on detector 100 when the lumen is empty than when the lumen is filled with fluid, as shown in FIG. 5(B).

The output signal produced by light detector 100 is applied to an amplifier 101, wherein it is amplified. The resulting amplified signal is applied to an intensity control circuit 102, wherein it is utilized to vary the output of a light source to control the light output of light source 60.

In operation, intensity control circuit 102 decreases the light output of light source 60 as the output of the second light detector 100 increases. This has the effect of reducing the light incident on light detector 61 below the level it would be at if the intensity control circuit was inoperative, thereby increasing the net change in signal level available for controlling operation of the metering apparatus. Although the signal incident on the second light detector 100 also falls with reduction in light output from light source 60, the gain provided to the output of detector 100 by amplifier 101 and intensity control circuit 101 is sufficient to overcome this reduction and achieve a net increase at the output of detector 61.

Figure 6:
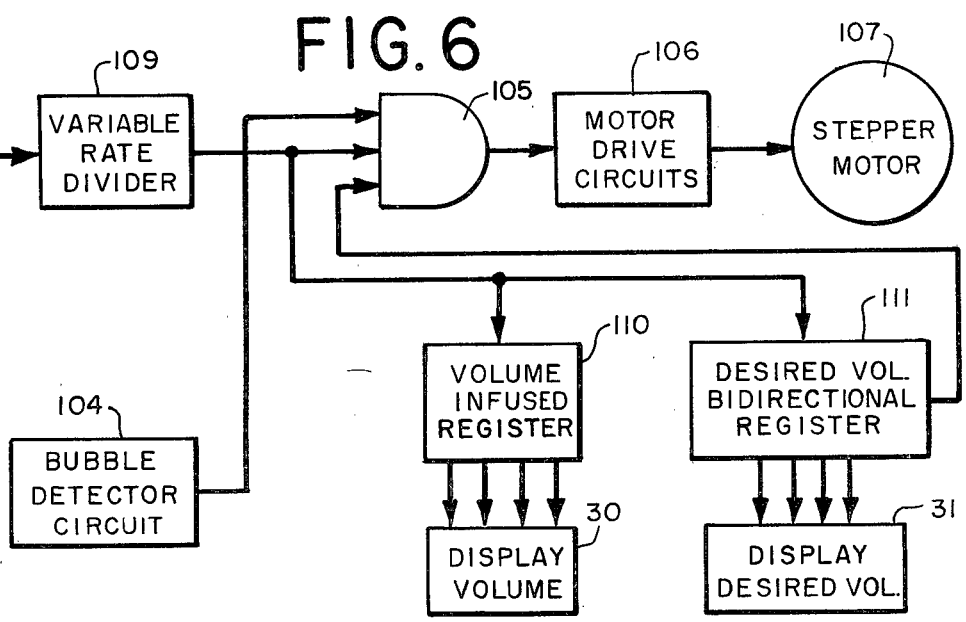
FIG. 6 is a simplified functional block diagram of the control system of the metering apparatus of FIG. 1.

The output of light detector 61 is applied to a detector circuit 104 wherein it is utilized to develop a control signal suitable for controlling the operation of the metering apparatus. Referring to FIG. 6, in the present embodiment the output of bubble detector circuit 104 is applied to one input of an AND gate 105, wherein it serves to control the application of control pulses to the motor drive circuit 106 of a stepper motor 107, which is utilized to drive the pump rotor 40 of the apparatus.

Control pulses for drive circuit 106 are obtained from a pulse source in the form of a clock 108. The clock pulses are divided to a lower frequency by a a variable-rate divider 109, and applied through AND gate 105 to the motor drive circuit. The division factor of rate divider 109 is selected by the operator to obtain a desired rate. The pulses derived from divider 109 are also applied to a volume register 110 wherein they are counted for use by volume display 30. The divided pulses are also applied to a bi-directional register 111 which supplies an inhibit signal to AND gate 105 upon the desired volume having been infused. The counting state of the register are displayed by the display 31.

Referring to FIG. 7, a preferred form of bubble detector circuit 104 may comprise a multivibrator 121 consisting of three NAND gates 122, 123 and 124. A capacitor 125 connected to the output of gate 123 and a potentiometer 126 connected to the output of gate 124 provide an RC time constant circuit which determines the frequency of the multi-vibrator output signal in a manner well known to the art. A diode 127 is connected between the arm of potentiometer 126 and the output of gate 124 to vary the duty cycle of the oscillator output signal. A fixed resistance 128 connected in series with the body of potentiometer 126 provides a desired adjustment range.

The AC signal generated by multi-vibrator 121 is applied through a resistance 129 and transistor 130 to light source 60. The AC signal developed by multi-vibrator 121 is amplified by transistor 130 and utilized to drive the LED, causing the LED to produce a light output which varies at a rate dependent on the output frequency of the multi-vibrator.

The alternating light developed by the LED is converted by phototransistor detector 132 to an output signal indicative of the strength of the transmitted light. The emitter of transistor 133 is connected to ground through a resistor 134, and is connected through respective diodes 135–137 to respective inputs of a threshold trigger device in the form of a dual Schmidt trigger 138. The cathodes of diodes 135–137 are connected to ground by respective parallel combinations of capacitors 140–142 and resistors 143–145. These elements serve in conjunction with the diodes as alternating current detectors, generating a DC signal at the inputs of trigger 138 dependent on the amplitude of the AC signal produced by detector 61. The dual Schmidt trigger 138, which may be a commercially available component such as the type NC14583B Schmitt trigger marketed by Motorola, Inc., of Schaumburg, IL, produces an output upon reduction of either of its input signals falling below a predetermined threshold level. The input associated with diode 135 functions as an enabling input for both triggers. The outputs of Schmidt triggers 138, which comprise a first control signal, are applied to one input of a logic OR gate 139.

The emitter of transistor 133 is also connected to ground through series-connected resistors 146 and 147. The signal developed at the junction of these two resistors is filtered by a series-connected resistor 148 and a short-connected capacitor 149 and resistor 150 connected to ground. This forms a second control signal, which is applied to the remaining input of OR gate 139. In this way, OR gate 139 is provided with the output signal developed by the dual Schmitt trigger 138; and with the DC control signal developed across capacitor 149, either of which can result in an output from the gate in the event of the occurence of a bubble in tubing 16. The output of Schmitt triggers 138 and the output of OR gate 139 are also connected to the positive unidirectional current source of the system by respective resistors 153 and 154.

Since the output of OR gate 139 is dependent on both the amplitude of the AC signal as rectified and applied to the parallel-connected Schmitt triggers 138, and on the DC signal developed across capacitor 149, the bubble detector utilized in the metering apparatus provides two control channels. The first channel, which utilizes Schmitt triggers 138, establishes a highly precise threshold below which an alarm output is produced. The second channel, which depends only on the input characteristic of gate 139, serves to provide an alarm output in event of failure of resistor 134 in the photodetector bias circuit.

In order for bubble detector 62 to not provide an output, it is necessary that the DC signals applied to the Schmitt triggers as a result of rectification by diodes 136 and 137 be above a predetermined minimum level, which is possible only when there is fluid within tubing segment to provide a lens to direct light from light source 60 to light detector 61.

While a particular embodiment of the invention has been shown and described, it will be obvious to those skilled in the art that changes and modifications may be made therein without departing from the invention in its broader aspects, and therefore, the aim in the appended claims is to cover all such changes and modifications as fall within the true spirit and scope of the invention.

We claim:

1. A bubble detector for signaling the occurrence of a fluid absence in a fluid administration set, of the type having a transparent tubing segment of generally cylindrical cross section, said bubble detector comprising, in combination:

a light source arranged at one side of the tubing segment:

a first light detector generally arranged at the opposite side of the tubing segment opposite said light source and defining in conjunction with said light source a light path through the tubing segment, said first detector generating a first output signal indicative of the intensity of light from said light source incident thereon, the intensity of said incident light increasing in the presence of fluid within the lumen of the tubing segment as a result of the focusing effect thereof;

a second light detector generally arranged at an angle to said light path, said second detector generating a second output signal indicative of the intensity of light from said light source incident thereon, the intensity of said incident light decreasing in the presence of fluid within the lumen of the tubing segment as a result of the focusing effect thereof;

detector circuit means responsive to said first detector output signal for providing an alarm signal upon the intensity of the light incident on said first light detector falling below a predetermined minimum level; and intensity control means responsive to said second detector output signal for decreasing the light output of said light source upon the light incident on said second detector increasing to increase the effectiveness of said control circuit means in responding to the absence of fluid in the lumen 2. A bubble detector as defined in claim 1 wherein said second light detector is disposed at an angle to said light path generally on the opposite side of said tubing segment from said light source.

3. A bubble detector as defined in claim 3 wherein said angle is approximately from 35° to 45° to said light path at the axis of the tubing segment.

4. A bubble detector as defined in claim 1 wherein said light path between said light source and said first light detector extends through the axis of the tubing segment.

5. A bubble detector as defined in claim 1 including a power source for said light source, said intensity control means acting to modulate the output of said power source to control the light output of said light source.

6. A bubble detector for signaling the occurrence of a fluid absence in a fluid administration set of the type having a transparent tubing segment, said bubble detector comprising, in combination:

a light source arranged at one side of the tubing segment;

a first light detector generally arranged at the opposite side of the tubing segment opposite said light source and defining in conjunction with said light source a light path extending through the axis of the tubing segment, said first detector generating a first output signal indicative of the intensity of light from said light source incident thereon, the intensity of said incident light increasing in the presence of fluid within the lumen of the tubing segment as a result of the focusing effect thereof;

a second light detector generally arranged on the opposite side of the tubing segment at an angle to said light path, said second detector generating a second output signal indicative of the intensity of light from said light source incident thereon, the intensity of said incident light decreasing in the presence of fluid within the lumen of the tubing as a result of the focusing effect thereof;

detector circuit means responsive to said first detector output signal for providing an alarm signal upon the intensity of the light incident on said first light detector falling below a predetermined minimum level; and intensity control means responsive to said second detector output signal for decreasing the light output of said light source upon the light incident on said second detector increasing to increase the effectiveness of said control circuit means in responding to the absence of fluid in the lumen of the tubing segment.

7. A bubble detector for signaling the occurrence of a fluid absence in a fluid administration set of the type having a transparent tubing segment of generally cylindrical cross-section, a bubble detector comprising, in combination:

a light source arranged at one side of the tubing segment;

a power source for said light source;

a first light detector generally arranged at the opposite side of the tubing segment opposite said light source and defining in conjunction with said light source a light path through the tubing segment, said first detector generating a first output signal indicative of the intensity of light from said light source incident thereon, the intensity of said incident light increasing in the presence of fluid within the lumen of the tubing segment, as a result of the focusing effect thereof;

a second light detector generally arranged at an angle to said light path, said second detector generating a second output signal in response to the intensity of light from said light source incident thereon, the intensity of said incident light decreasing in the presence of fluid within the lumen of the tubing segment as a result of the focusing effect thereof;

detector circuit means responsive to said first detector output signal for providing an alarm signal upon the intensity of the light incident on said first light detector falling below a predetermined minimum level; and intensity control means responsive to said second detector output signal for decreasing the output of said power source as applied to said light source upon the light incident on said second detector increasing to increase the effectiveness of said control circuit means in responding to the absence of fluid in the lumen of the tubing segment.

* * * * *

UNITED STATES PATENT AND TRADEMARK OFFICE
CERTIFICATE OF CORRECTION

PATENT NO. : 4,344,429

DATED : August 17, 1982

INVENTOR(S) : John E. Gupton and Norm Shim

It is certified that error appears in the above-identified patent and that said Letters Patent are hereby corrected as shown below:

Column 8, line 18, after the word "lumen" add the following:

"of the tubing segment."

Claim 3 depends from Claim 2.

Signed and Sealed this

Twelfth Day of October 1982

[SEAL]

Attest:

Attesting Officer

GERALD J. MOSSINGHOFF

Commissioner of Patents and Trademarks